US006613556B1

United States Patent
Eckels et al.

(10) Patent No.: US 6,613,556 B1
(45) Date of Patent: Sep. 2, 2003

(54) ADAPTATION OF VIRUS TO VERTEBRATE CELLS

(75) Inventors: Kenneth H. Eckels, Rockville, MD (US); Joseph R. Putnak, Silver Spring, MD (US); Bruce L. Innis, Haverford, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/534,724

(22) Filed: Mar. 24, 2000

Related U.S. Application Data

(60) Provisional application No. 60/126,316, filed on Mar. 26, 1999, and provisional application No. 60/182,065, filed on Feb. 11, 2000.

(51) Int. Cl.$^7$ .................................................. C12N 7/00
(52) U.S. Cl. .............................. 435/235.1; 435/91.33; 424/204.1; 424/218.1
(58) Field of Search .............................. 424/9.2, 204.1, 424/218.1; 435/91.33, 235.1

(56) References Cited

PUBLICATIONS

Smith et al. 1985 J. Gen. Virol. pp. 559–571.*
Kraiselburd et al 1987 Publication GRAI8723.*
Osatomi, K., "Complete Nucleotide Sequence of Dengue Type 3 Virus Genome RNA", Virology 176:643–647 (1990).
Puri, B., "Molecular analysis of dengue virus attenuation after serial passage in primary dog kidney cells", J. General Virology (1997) 78:2287–2291.
Botstein and Shortle, 1985, "Strategies and applications of in vitro mutageNesis", Science, vol. 229, No. 4719, pp. 1193–1201.
Clarke and Casals, 1958, "Techniques for hemagglutination and hemagglutination–inhibition with arthropod–borne viruses", Am. J. Trop. Med. Hyg., 7, 561–573.
Halstead et al., 1984, "Selection of attenuated Dengue 4 viruses by serial passage in primary kidney cells," Am. J. Trop. Med. Hyg. 33(4), pp. 654–665.
Halstead et al., 1984, "Selection of attenuated Dengue 4 viruses by serial passage in primary kidney cells," Am J. Trop. Med. Hyg, 33(4), pp. 666–671.
Halstead et al., 1984, "Selection of attenuated Dengue 4 viruses by serial passage in primary kidney cells," Am J. Top. Med. Hyg, 33(4), pp. 672–678.
Halstead et al., 1984, "Selection of attenuated Dengue 4 viruses by serial passage in primary kidney cells," Am J. Trop. Med. Hyg, 33(4), pp. 679–683.
Hayflick, 1988, "History of cell substrates used for human biologicals", Symposium on Continuous Cell Lines as Substrates for Biologicals, Arlington, Virginia, USA, pp. 11–26.
Hoke et al., 1990, "Preparation of an attenuated Dengue 4 virus vaccine", Am J. Top. Med., Hyg., 43(2), pp. 219–226.
Marchette, 1990, "Preparation of an attenuated Dengue 4 virus vaccine", Am J. Top. Med. Hyg., 43(2), pp. 212–218.
Mizrahi, ed., Viral Vaccines, "WHO Attitude to Viral Vaccines", Wiley–Liss, New York (1990), pp. 39–60.
Putnak et al, 1996, "Development of a purified inactivated, Dengue–2 virus, vaccine prototype in vero cells: immunogenecity and protection in mice and Rhesus monkeys," J. Infectious Dis., 174, pp. 1176–1184.
Russell, et al., "A plaque reduction test for dengue virus neutralizing antibodies", J. Immunology, vol. 99, No. 2, 1967, pp. 285–290.
Scott, 1983, "Dengue 2 vaccine: Dose response in volunteers in relation to yellow fever immune status," J. Infectious Diseases, vol. 148, No. 6, pp. 1055–1060.
Sukhavachana et al, 1966, "Tissue culture techniques for the study of dengue viruses", Abreges des Communications, Bull. WHO 35, pp. 65–66.
Zollerf and Smith, 1984, Laboratory Methods, "Oligonucleotide–directed mutagenesis: a simple method using two oligonucleotide primers and a single–stranded DNA template", DNA, vol. 3, No. 6, pp. 479–488.
Bhamarapravati, 1987, "Immunization with a live attenuated dengue–2–virus candidate vaccine: clinical, immunolgical and biological responses in adult volunteers", Bull. WHO, 65(2), pp. 189–195.
Conrad et al., "Infection with Nippostrongylus Brasiliensis or injection of anti–IgD antibodies markedly enhances Fc–receptor–mediated interleukin 4 produciton by non–B, non–T Cell,", J. Exp. Med., vol. 171, pp. 1497–1508.
Dharakul, et al., "Dengue virus–specific memory T cell responses in human volunteers receiveing a live attenuated dengue virus Type 2 candidate vaccine", J. Infect. Dis., vol. 170, pp. 27–33.
Edelman et al., "A live attenuated Dengue–1 vaccine candidate passaged inprimary dog kidney cell cultures is attenuated and immunogenic for humans", 1994, Am. J. Trop. Med. Hyg., 170, pp. 1448–1455.
Halstead, 1978, "Studies on the attenuation of Dengue 4", Asian J. Infectious Dis., vol. 2, pp. 112–117.
Halstead, 1970, "Long 'cure 'improves results of pig heterograft heart valves," JAMA, vol. 211, No. 6, pp. 911–916.
Johnson and Roehrig, "New mouse model for Dengue virus vaccien testing", J. Virology, Jan. 1999, vol. 73, No. 1, pp. 783–786.

(List continued on next page.)

Primary Examiner—Lynette R. F. Smith
Assistant Examiner—Robert A. Zeman
(74) Attorney, Agent, or Firm—Elizabeth Arwine

(57) ABSTRACT

The present invention provides a method for replicating virus to high titer in cultured mammalian cells by infecting the mammalian cells with the high titer virus strain to obtain infected cells, specifically, attenuated dengue virus strains of serotype 1, 2, 3, and 4. The resulting replicated virus is suitable for use in vaccines and vaccination methods which are also provided by the invention.

5 Claims, 2 Drawing Sheets

OTHER PUBLICATIONS

Kontny et al., "Gaamma interferon augments Fcy receptor–mediated Dengue virus infection of human monocytic cells", J. Virology, Nov. 1988, vol. 62 No. 11, pp. 3928–3933.

Kurane et al., "Dengue virus–specifiic human T cell clones", J. Exp. Med., vol. 170, 1989, pp. 763–775.

Kurane et al., "Activation of T lymphocytes in dengue virus infections", J. Clin. Invest., vol. 88, 1991, pp. 1473–1480.

Kurane et al., "T cell activation in vivo by Dengue virus infection", J. Clin. Lab. Immunol., 1995, vol. 46, pp. 35–40.

Peters, "Actions of cytokines on the immune response and viral interactions: an overview", Hepatology, vol. 23, 1996, pp. 909–916.

Sittisombut et al., "Lack of augmenting effect of interferon–y on Dengue virus multiplication in human peripheral blood monocytes", J. Medical Virology 45:43–49, 1995.

Sabin, 1959, "Dengue", Viral and Rickettsial Infections of Man, Philadelphia: JB Lippincott Company, pp. 361–373.

Simmons et al., "Experimental Studies of Dengue", 1931, Manila BUreau of Printing, pp. 1–489.

Wisseman and Sweet, "Immunolgical studies with Group B arthropod–borne viruses", Am J. Trop. Med. Hyg., vol. 11, pp. 570–575 (1962).

Yuill et al., "Dengue–virus recovery by direct and delayed plaques in LLC–MK2 cells", Am. J. Trop. Med. Hyg., vol. 17, 1968, pp. 441–448.

Smith and Wright, "Synthesis of Proteins and Glycoproteins in Dengue Type 2 Virus–Infected Vero and Aedes albopictus Cells", J. Gen. Virol., (1985) 66: 559–571.

Kraiselburd, E., "Comparative Infectivity Determination of Candidate Live Dengue Virus Vaccine in Monkeys, Mosquitoes and cell cultures", Annual and Final Report, May 1987, pp. 1–20.

Edelman, et al., "A Live Attenuated Dengue–1 Vaccine Candidate (45AZ5) Passaged in Primary Dog Kidney Cell Culture SIs Attenuated and Immunogenic for Humans", J. Infectious Diseasees, 1994:170:1448–1455 (Dec.).

Angsubharkorn et al., "Dengue–3 (16562) PGMK 33 Vaccine: Neurovirulence, Viremia and Immune Responses in Macaca Fascicularis", Southeast Asian J. Trop. Med. Public Health, vol. 25, No. 3, Sep. 1994.

(XP–002150293) Sun et al., Program Abstracts from the First Annual Conference on Vaccine Research, May 30–Jun. 1, 1998, "Phase I Study of Two Doses of Monovalent Live–Attenuated Dengue Virus Vaccines" (2 pages).

Vaughn, et al., "Testing of a dengue 2 live–attenuated vaccine (strain 16681 PDK 53) in ten American volunteers", Vaccine, vol. 14, No. 4, pp. 329–336, 1996.

* cited by examiner

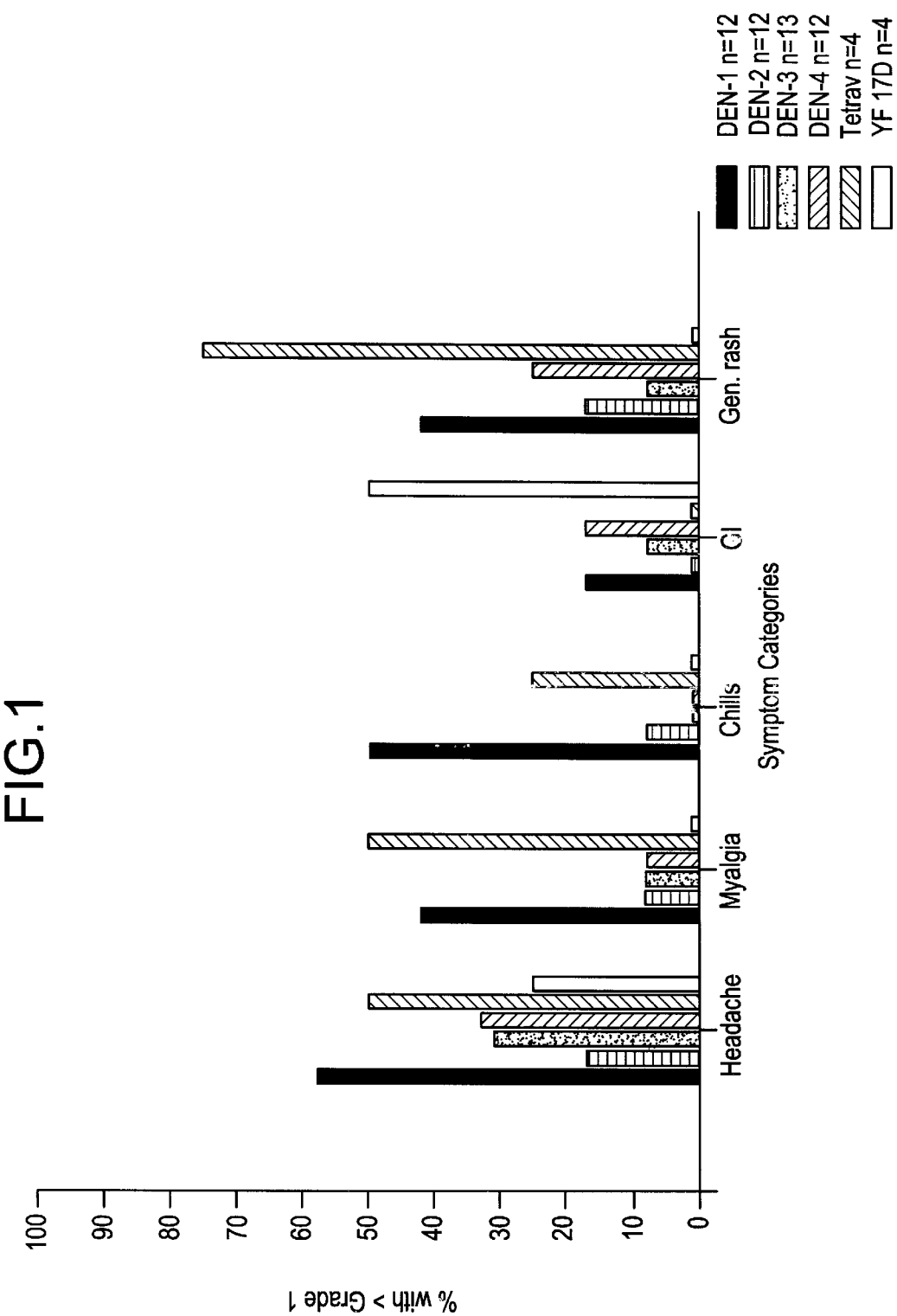

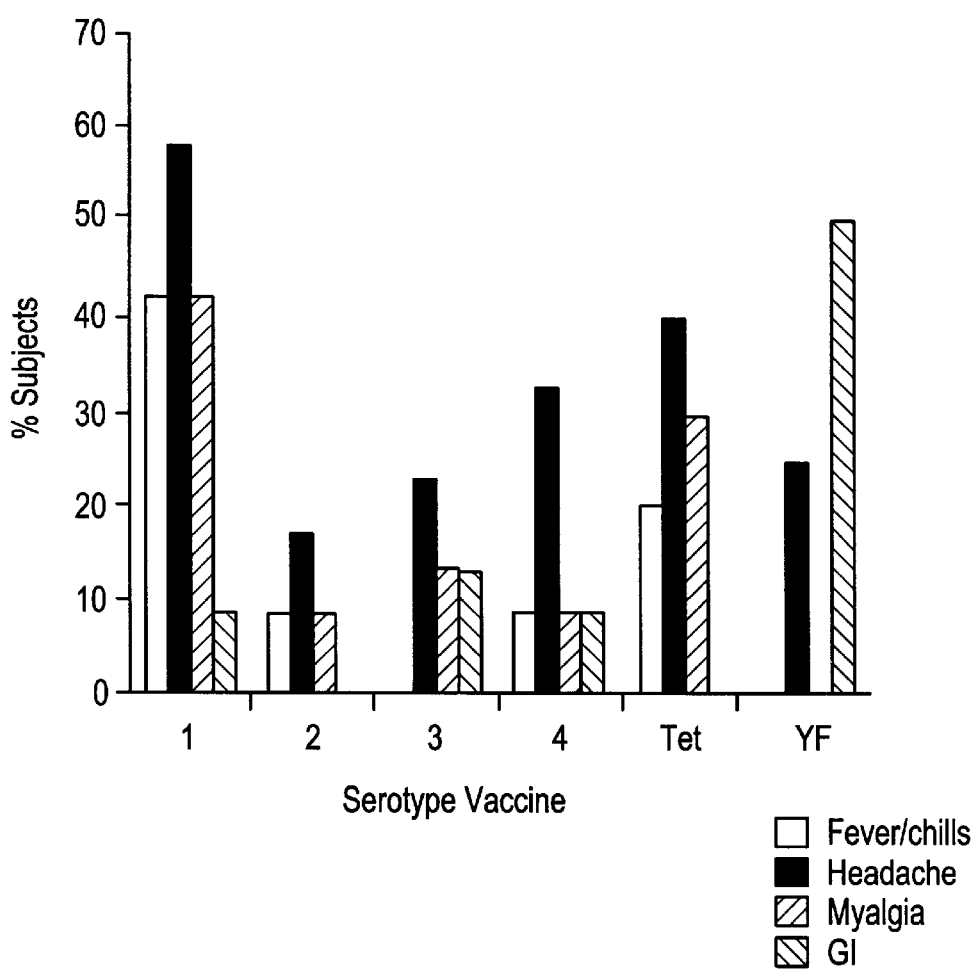

ADAPTATION OF VIRUS TO VERTEBRATE CELLS

This application claims the benefit of priority under 35 U.S.C. §119(e) from U.S. application Ser. No. 60/126,316 filed on Mar. 26, 1999, and U.S. application Ser. No. 60/182,065 filed on Feb. 11, 2000.

FIELD OF THE INVENTION

This invention relates to virus replicated in vertebrate cell cultures, which are suitable for use in vaccine production. Viral strains useful as vaccines can be adapted to vertebrate cells by serial passage and optimization of replication of the vaccine strains. Vaccine strains adapted for growth in vertebrate cells offer many advantages. The invention also relates to methods for making and using such replicated viruses such as for vaccine.

BACKGROUND OF THE INVENTION

Cultured vertebrate cells have been used for virus replication and have been classified into at least three distinct groups. Primary cells, derived from normal tissue; diploid cell strains are those that have a limited, finite life span, depending on the species of origin; and continuous cell lines, cultured cells that replicate indefinitely and may be capable of growth in suspension culture. Hayflick, in *Continuous Cell Lines as Substrates for Biologicals*, Arlington, Va., p2 (1988).

At present most viral vaccines are produced using primary cells or diploid cell strains. Species of origin include monkeys, chicken, embryos, and hamsters. These cell cultures have certain advantages such as easy preparation using simple media and bovine sera and sensitivity to a wide range of viruses. However, primary cells suffer from disadvantages, such as contamination by various adventitious agents, variable quality and sensitivity, and difficulty in obtaining suitable tissue for cell cultivation, low virus titers and the high cost of obtaining and preparing such cell cultures. Diploid cell strains have many of the same disadvantages as well as a finite life span that limits expansion of the cells.

African green monkey kidney (Vero) cells are a continuous cell line, that is not tumorigenic, and is suitable and advantageous for human vaccine production. In fact, several licensed vaccines are currently manufactured in these cells. Vero cells, and possibly other continuous cell lines, may be suitable for dengue virus vaccine production. However, it is not known whether the antigenic characteristic of a vaccine virus strain would not be altered after passaging in a continuous cell line.

SUMMARY OF THE INVENTION

The present invention relates to methods, replicated viruses and vaccine compositions using high growth strains of dengue virus.

The invention thus provides for a method for increasing dengue viral replication in culture by passaging the desired viral strain in continuous vertebrate cells and choosing the viral strain which replicates to high titer as the seed strain. When the dengue strain is attenuated, the resulting seed strain can be suitable for production of vaccine.

Preferably, the vertebrate host cells are continuous cell cultures derived from epithelial cells or fibroblasts, as mammalian cell lines of passage number 10–250. Preferably used for vaccine production are Vero cells as a continuous line of a passage number of about 20–250, currently available and certified (e.g., by the WHO).

Dengue virus of the invention, in isolated, purified or concentrated from, preferably has an infectivity titer of about $10^6$–$10^9$ (such as $10^6$–$10^7$, $10^7$ and $10^8$–$10^9$, or any range or value therein) plaque forming units (PFU) per ml.

The present invention also provides vaccine compositions comprising at least one strain of a dengue virus of any of the four serotypes of dengue of the present invention, in inactivated or attenuated form, optionally further comprising at least one of: (a) at least one pharmaceutically acceptable carrier or diluent; (b) at least one adjuvant and/or (c) at least one therapeutic agent.

The present invention also provides a method for eliciting an immune response to at least one dengue virus strain in a mammal, which response is prophylactic or therapeutic for a dengue virus infection. The method comprises administering to the mammal a vaccine composition comprising an inactivated and/or attenuated dengue virus of the present invention. The composition is provided in an amount that is protective or therapeutic for the mammal against a dengue virus pathology caused by infection with dengue virus.

Other objects, features, advantages, utilities and embodiments of the present invention will be apparent to skilled practitioners from the following detailed description and examples relating to the present invention.

BRIEF DESCRIPTION OF THE DRAWINGS

FIG. 1: Occurrence of >Grade 1 symptoms as a result of vaccine administration.

FIG. 2: Frequency of distribution of reactogenicity index by serotype.

DETAILED DESCRIPTION

The present invention provides dengue virus using continuous mammalian cell lines. The viruses used for generating the replicated virus are high titer strains, virulent or attenuated, of at least one dengue virus serotype. Dengue viruses are grouped into four serotypes, serotype 1–4. When using attenuated strains, the replicative dengue virus will be suitable for vaccine production.

The term "high titer virus" as used herein is defined to produce high infectivity titers in in vitro tissue culture replication systems, such as $10^5$–$10^{10}$ PFU/ml, and preferably $10^6$–$10^9$ PFU/ml.

The screening of dengue virus for use in replication or vaccine production can be assayed using any known and/or suitable assay, as is known in the art. Such assays (alone or in combination) that are suitable for screening include, but are not limited to, viral replication, quantitative and/or qualitative measurement of antigen, transcription, replication, translation, virion incorporation, virulence, viral yield, using such methods as reverse genetics, complementation, and/or infection. For example, virus replication assays can be used to screen for attenuation or inactivation of the virus. Please see Sukhavachana et al., 1966, Bull WHO 35, 65–66 for examples of these assays. All documents cited herein supra or infra are hereby incorporated in their entirety by reference thereto.

According to the present invention, any dengue isolate of any serotype can be used to obtain high titer strains suitable for replicating in vertebrate host cells, in order to provide replicated dengue virus of the invention. The clinical isolate can be made into a high growth strain by multiple passages of the clinical isolate in continuous vertebrate cell lines, with selection of high titer variants.

According to methods for replicating viruses of the present invention, suitable vertebrate host cells can be used, including Vero cells or other vertebrate cells suitable with respect to excluding adventitious agents, preferably of a suitable passage number that can be certified according to the WHO requirements for vaccine production (Mizrahi, ed., *Viral Vaccines*, Wiley-Liss, New York (1990), pp. 39–60). Non-limiting examples of cell lines that can be suitable for methods, viruses and compositions used in the present invention, include, but are not limited to, mammalian fibroblast or epithelial cells as continuous cell lines. Further non-limiting examples include Vero, MDBK, BK-21, MDCK (Madin Darby canine kidney), CHO (Chinese hamster ovary) and CV-1 cells, readily available from commercial sources (e.g., ATCC, Va). Vero cells of passage number less than 191 are preferred, or any range or value therein.

It is preferred that the replicated virus produced in continuous cell lines is highly purified prior to vaccine formulation according to the invention. Generally, the purification procedures will result in the extensive removal of cellular DNA, other cellular components, and adventitious agents. Procedures that extensively degrade or denature DNA can also be used. See, e.g. Mizrahi, 1990, supra.

Described in the examples are four serotypes suitable for vaccine use in humans. The dengue viruses described herein were produced by serial passaging of an infectious dengue virus isolate in a suitable host cell line such as primary dog kidney cells so that mutations accumulate that confer attenuation on the isolate. Serial passaging refers to the infection of a cell line with a virus isolate, the recovery of the viral progeny from the host cells, and the subsequent infection of host cells with the viral progeny to generate the next passage.

Preferably, the following attenuated viruses are used in the methods of the invention to produce replicative virus in continuous cell culture even though other virus compositions, of any of the serotypes, can be used.

1) The attenuated dengue-1 virus, derived from 45AZ5 isolate, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2648.

2) The attenuated dengue-2 virus strain S16803, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2653.

3) The attenuated dengue-3 virus strain CH53489, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2647.

4) The attenuated dengue-4 virus, strain 341750, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2652.

Serial passaging of a virulent (disease-causing) strain of dengue results in the isolation of modified virus which may be attenuated, i.e., infectious, yet not capable of causing disease. These modified viruses are tested in monkeys for reduced infectivity. Those that have reduced infectivity are subsequently tested in humans. Humans are the only primate that will exhibit signs of clinical disease. The viruses that show minimal to no clinical reactivity but still infect and induce an immune response are chosen.

For the preparation of the attenuated dengue virus serotypes 1–4 above, various passages in the series were tested for clinical effect after final passage in fetal Rhesus monkey lung cells (FRhL). FRhL cells were used to optimize virus titers wherein, in general, passage 1 was considered the master seed, passage 2 was considered the production seed, and passage 3 was considered the vaccine lot. Vaccines were prepared at various PDK passage levels, and the vaccine products tested for attenuation in monkeys and humans. The virulence of a passaged virus, i.e., the ability to cause disease, was assessed by daily monitoring of symptoms such as temperature (fever), headache, rash, to name a few. The passage was considered attenuated, as judged by the inability of this virus to elicit clinical signs of dengue disease in vaccinees.

Propagation of the attenuated viruses of the invention may be in a number of cell lines which allow for high titer dengue virus growth. Highest virus yields are usually achieved with Vero cells. Cells are typically inoculated at a multiplicity of infection ranging from about 0.01 to 0.005, and are cultivated under conditions permissive for replication of the virus, e.g., at about 30–37° C. and for about 3–5 days, or as long as necessary for virus to reach an adequate titer. Virus is removed from cell culture and separated from cellular components, typically by well known clarification procedures, e.g., gradient centrifugation and column chromatography, and may be further purified as desired using procedures well known to those skilled in the art. Preferably, care must be taken to maintain temperature of 2–10° C. during purification to maintain viability of the virus.

The isolation of a high titer virus may be followed by a sequence analysis of its genome to determine the basis for the high titer phenotype. This is accomplished by sequencing the viral DNA or RNA and identifying nucleotide changes in the high titer isolate relative to the genomic sequence of a control virus. Therefore, the molecular changes that confer high titer growth on a strain can be characterized.

One embodiment of the invention provided herein, includes the introduction of sequence changes at any of the positions listed in the table above, alone or in combination, in order to generate high titer virus progeny. Viral genomes with such alterations can be produced by any standard recombinant DNA techniques known to those skilled in the art (Ausubel et al., *Current Protocols in Molecular Biolocry*, Greene Publishing Associates & Wiley Interscience, New York, 1989) for introduction of nucleotide changes into cloned DNA. A genome may then be ligated into an appropriate vector for transfection into host cells for the production of viral progeny.

The ability to generate viral progeny through plasmid-mediated introduction of a viral genome can also be used to produce viruses with defined molecular changes. In this embodiment of the invention, stable virus stocks can be produced that contain altered sequences that confer desired properties on the virus, for example, high titer growth. This approach can also be used to assess the effect of molecular changes on various properties of the virus, i.e. antigenic type, virulence, or attenuation by introducing desired sequence changes into the viral genome, producing virus progeny from the genome, and recovering the virus progeny for characterization. In addition, this approach can be used to construct a virus with heterologous sequences inserted into the viral genome that are concurrently delivered by the virus to generate an immune response against other diseases.

Construction of viral genomes with defined molecular changes can be accomplished using standard techniques such as oligonucleotide-directed, linkerscanning or polymerase chain reaction-based mutagenesis techniques known to those skilled in the art (Zoller and Smith, 1984, *DNA* 3, 479–488; Botstein and Shortle, 1985, *Science* 229, 1193). Ligation of the genome into a suitable vector for transfer may be accomplished through standard techniques known to those skilled in the art. Transfection of the vector into host cells for the production of viral progeny may be done using any of the standard techniques such as calcium-phosphate or DEAE-dextran mediated transfection, electroporation, protoplast fusion, and other techniques known to those skilled in the art (Sambrook et al., *Molecular Cloning: A laboratory Manual*, Cold Spring Harbor Laboratory Press, 1989).

For vaccine use, the attenuated high titer dengue viruses of the invention can be used directly in vaccine formulations, or lyophilized, preferably in a stabilizer (Hoke, 1990, Am J Trop Med Hyg 43, 219–226), as desired, using lyophilization protocols well known to the artisan. Lyophilized virus will typically be maintained at about 4° C. When ready for use, the lyophilized virus is reconstituted in water, or if necessary, in a stabilizing solution, e.g., saline or comprising $Mg^{++}$ and HEPES, with or without adjuvant, as further described below.

Thus, dengue virus vaccines of the invention contain as an active ingredient an immunogenically effective amount of more than one attenuated high titer dengue virus chosen from the group consisting of dengue-1, dengue-2, dengue-3, and dengue-4 as described herein. The attenuated high titer virus composition may be introduced into a subject, particularly humans, optionally with a physiologically acceptable vehicle and/or adjuvant. Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxilliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Administration of the high titer live attenuated viruses disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. As a result of the vaccination, the host becomes at least partially or completely immune to dengue virus infection of the serotypes administered, or resistant to developing moderate or severe dengue viral infection.

The vaccine composition containing the attenuated dengue viruses of the invention are administered to a person susceptible to or otherwise at risk of dengue virus infection to enhance the individual's own immune response capabilities. Such an amount is defined to be an "immunogenically effective dose". In this use, the precise amount again depends on the subject's state of health and weight, the mode of administration, the nature of the formulation, etc., but generally range from about $10^4$ to $10^5$ pfu virus per subject. When the four serotypes are combined, a preferred composition comprises optimal formulations of each of the serotypes. In any event, the vaccine formulations should provide a quantity of attenuated dengue virus of each of the serotypes sufficient to effectively protect the subject against serious or life-threatening dengue virus infection.

The attenuated dengue viruses of the invention of one particular serotype can be combined with attenuated viruses of other serotypes of dengue virus to achieve protection against multiple dengue viruses. Typically the different modified viruses will be in admixture and administered simultaneously, but may also be administered separately.

In some instances it may be desirable to combine the attenuated dengue virus vaccines of the invention with vaccines which induce protective responses to other agents.

Single or multiple administration of the vaccine compositions of the invention can be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection.

The following examples are provided by way of illustration, not limitation.

The following MATERIALS AND METHODS were used in the examples that follow.

Materials and Methods for Vaccine Production

Virus Strains.

DEN viruses were passaged in primary dog kidney (PDK) cell cultures following isolation from human and mosquito sources. Table 1 lists the strains that were adapted and passaged in PDK cells. After passage in PDK cells, virus strains were further adapted to FRhL cells for seed and vaccine production. This consisted of an additional 3–4 passages for final vaccine lot preparation. Parental virus strains, also listed in Table 1, were derived from low, cell culture passages in cells that were permissive for DEN virus replication.

Vaccine Production.

DEN vaccines for all four serotypes were prepared in FRhL cell culture using a similar procedure. FRhl cells, banked and pre-tested (see Table 2 for testing results) were removed from liquid nitrogen storage and plated in 150 $cm^2$ flasks in Eagle's minimum essential media (EMEM) (Biowhittaker, Waldersville, Md.) cell medium supplemented with non-essential amino acids, fetal. bovine serum, FBS (2%) (Biowhittaker, Waldersville, Md.), and antibiotics. After the flasks reached confluency, medium was removed and flasks inoculated with DEN production seed diluted for an input of 0.01 MOI, and allowed to adsorb at 32° C. for 1 hr. Following adsorption and feeding with fresh EMEM medium, flasks were returned to 32° C. for 4 days. On day 4 post-inoculation, medium from all flasks was discarded and cell monolayers were washed 3 times with 100 ml of Hanks BSS (Biowhittaker, Waldersville, Md.). After washing, flasks were fed with EMEM medium containing 0.25% human serum albumin (HSA, Alpha Therapeutic Corp, Los Angeles, Calif.) replacing FBS. After an additional two days of incubation at 32° C., supernatant culture fluids were removed from all flasks and pooled. After sampling for safety tests, the remaining culture fluids were pooled and clarified by filtration through a 0.45 micron, non-protein binding membrane filter. The filtered fluids were pooled and mixed with an equal volume of stabilizer containing 15% lactose and 5% HSA. The bulk, stabilized fluids were stored at −70° C. until freeze-dried. For final vialing, bulk, stabilized fluids were thawed rapidly at 41° C. and aliquoted in 3 ml volumes in serum vials. Trays of vials were frozen to a temperature of −40° C. in a Hull freeze-dryer, followed by drying for 1 day. Following capping, vials were stored at −20° C. in a monitored freezer.

Vaccine Testing.

All cell banks used for virus preparations as well as seed and vaccine lots were tested for the presence of contaminating agents. The test articles and results are listed in Table 2. No detectable contaminants were found in any of the products.

Rhesus Monkey Inoculation.

Adult, male and female rhesus monkeys (6–15 kg) were immunized with the DEN vaccine lots or parent viruses by subcutaneous inoculation of 0.5 ml in the upper arm. Blood for virus isolation and antibody tests was drawn from the femoral vein prior to inoculation and every day for 14 days following inoculation. Blood was also drawn at 30 and 60 days following immunization. Virus challenges were performed similarly.

Virus Isolation by Amplification in C6/36 Cells.

Virus isolation by C6/36 cell culture amplification has been described in Putnak et al, 1996 (J. Infect Dis 174, 1176–1184). Briefly, following inoculation of monkeys, daily blood specimens were obtained from days 1 to 14. Serum was separated and frozen at −80° C. For recovery of virus from sera, thawed sera were diluted 1:3 in cell culture medium and used to inoculate 25 $cm^2$ flasks containing monolayers of C6/36 mosquito cells. Following adsorption of virus, flasks were maintained at 28° C. in EMEM maintenance medium. After 7 days, medium was changed and flasks incubated an additional 7 days. On day 14 post inoculation, supernatant culture fluids were decanted and frozen at −80° C. after mixing with an equal volume of heat-inactivated fetal bovine serum (FBS). Frozen

TABLE 1

Dengue virus strains used for development of live-attenuated vaccines.

| Serotype | Original Isolate | Vaccine strain: passage from human isolate | PDK passages selected for vaccine prep | FRhL passages for seed and vaccine prep | Parental strain: passage from human isolate |
|---|---|---|---|---|---|
| DEN-1 (West Pac 74; 45AZ5) | Human isolate, Nauru, 1974 | 20 × FRhL (with plaque selection and mutagenization with 5AZ); vaccine prep'd at p-20 caused dengue fever in 2 vols | 10, 20, 27 | 1: master seed 2: production seed 3: vaccine lot | 9 × FRhL |
| DEN-2 (S16803) | Human isolate, Thailand, 1974 | 1 × mosquito; 4 × PGMK | 10, 20, 30, 40, 50 | 1: master seed 2: production seed 3: vaccine lot | 4 × PGMK; 2 × C6/36 |
| DEN-3 (CH53489) | Human isolate, Thailand, 1973 | 4 × PGMK; 5 × C6/36 | 10, 20, 30 | 1: master seed 2: production seed 3: vaccine lot | 4 × PGMK |
| DEN-4 (341750) | Human isolate, Columbia, 1982 | 1 × mosquito | 6, 10, 15, 20 | 1: pre-master seed (PDK-20 only) 2: master seed 3: production seed 4: vaccine lot | 1 × mosq; 5 × PGMK; 4 × FRhL |

TABLE 2

Pre-clinical testing of FRhl cell banks and DEN LAV seeds and vaccine lots.

| Test | FRhl cell banks | Master Seed | Production Seed | Vaccine (Bulk) | Vaccine (Final Container) |
|---|---|---|---|---|---|
| Sterility | x | x | x | x | x |
| Mycoplasma | x |  | x | x |  |
| RT | x |  | x |  |  |
| Hemadsorption | x |  | x | x |  |
| Cell culture safety (4 cell lines) | x |  |  | x |  |
| Embryonated egg safety | x |  |  |  |  |
| Animal safety: adult mice | x |  |  | x |  |
| Animal safety: suckling mice | x |  |  | x |  |
| Animal safety: guinea pigs | x |  |  | x |  |
| Animal safety: rabbits | x |  |  |  |  |
| Tumorgenicity | x | NA | NA | NA | NA |
| Karyology | x | NA | NA | NA | NA |
| Monkey safety: neurovirulence | NA |  | x (DEN-4) |  |  |
| Monkey infectivity/immunogenicity | NA |  | x |  |  |
| Monkey efficacy | NA |  |  |  | x (DEN-2, DEN-4) |
| Infectivity (plaque assay) | NA | x | x | x | x |
| General safety | NA |  |  | x | x |
| Residual moisture | NA |  |  |  | x |
| Reconstituted pH | NA |  |  |  | x |

TABLE 2-continued

Pre-clinical testing of FRhl cell banks and DEN LAV seeds and vaccine lots.

| Test | FRhl cell banks | Master Seed | Production Seed | Vaccine (Bulk) | Vaccine (Final Container) |
|---|---|---|---|---|---|
| Reconstituted osmolality | NA | | | | x |
| Endotoxin | NA | | | | x |
| Identity (DEN) | NA | x | x | | x |

TABLE 3

DEN virus strain sets adapted to PDK cells, used for inoculation of rhesus monkeys.

| DEN virus strain | Viruses | Inoc: PFU/0.5 ml | Mks viremic/Total (Mean days viremia) | Mk seroconverted/Total (GMT PRNT$_{50}$ at 1–2 mo post inoc) |
|---|---|---|---|---|
| DEN-1, 45AZ5 | PDK-0 (parent) | $3.3 \times 10^4$ | 4/4 (6.8) | 4/4 (760) |
| | PDK-10 (prod seed)* | $7.0 \times 10^4$ | 4/4 (4.75) | 4/4 (1030) |
| | PDK-20 (prod seed) | $1.7 \times 10^4$ | 4/4 (4.5) | 4/4 (640) |
| | PDK-27 (prod seed) | $1.8 \times 10^4$ | 0/4 (0) | 4/4 (50) |
| DEN-2, S16803 | PDK-0 (parent) | $5.0 \times 10^6$ | 4/4 (5) | 4/4 (600) |
| | PDK-10 (prod seed) | $3.8 \times 10^5$ | 4/4 (4.75) | 4/4 (570) |
| | PDK-20 (prod seed) | $2.2 \times 10^5$ | 4/4 (6.5) | 4/4 (920) |
| | PDK-30 (prod seed$^1$) | $4.4 \times 10^5$ | 2/3 (3.3) | 4/4 (640) |
| | PDK-30 (prod seed$^2$) | $2.1 \times 10^5$ | 3/3 (6.0) | 3/3 (640) |
| | PDK-40 (prod seed) | $1.0 \times 10^4$ | 2/4 (1) | 3/4 (90) |
| | PDK-50 (prod seed$^1$) | $2.6 \times 10^6$ | 2/4 (1) | 4/4 (310) |
| | PDK-50 (prod seed$^2$) | $5.9 \times 10^5$ | 3/4 (3.25) | 4/4 (280) |
| | PDK-50 (vaccine) | $1 \times 10^6$ | ND | 4/4 (270) |
| DEN-3, CH53489 | PDK-0 (parent) | $8.0 \times 10^3$ | 3/3 (3) | 3/3 (660) |
| | PDK-10 (prod seed) | $2.5 \times 10^6$@ | 2/3 (1.3) | 3/3 (150) |
| | PDK-20 (prod seed) | $1.0 \times 10^6$@ | 0/3 | 3/3 (130) |
| | PDK-30 (prod seed) | $9.3 \times 10^5$@ | 0/3 | 0/3 (<10) |
| DEN-4, 341750 | PDK-0 (parent) | $1.0 \times 10^3$ | 3/3 (4.7) | 3/3 (420) |
| | PDK-6 (prod seed) | $1.7 \times 10^5$ | 1/4 (0.5) | 4/4 (250) |
| | PDK-10 (prod seed) | $2.9 \times 10^5$ | 1/4 (1.3) | 2/4 (90) |
| | PDK-15 (prod seed) | $5.5 \times 10^4$ | 1/4 (0.25) | 2/4 (40) |
| | PDK-20 (prod seed) | $5.5 \times 10^4$ | 1/4 (0.25) | 2/4 (70) |
| | PDK-20 (vaccine) | $1.2 \times 10^5$ | 1/3 (0.3) | 3/3 (50) |

$^{1,2}$Two separate monkey experimental groups.
@Plaque assay performed in C6/36 cells.

specimens were later assayed for infectious virus by plaque assay.

Plague Assays.

Infectious virus was titrated from amplified viremia isolates or directly from monkey sera by plaque assay in Rhesus monkey kidney (LLC-Mk$_2$, ATCC CCL7) cells following the procedure of Sukhavachana et al. 1966 (Bull WHO 35, 65–66). Assays in C6/36 cells was performed as described in Putnak et al, 1996, supra.

Neutralization Tests.

DEN neutralizing antibodies were measured from monkey sera using a plaque reduction neutralization test similar to that used by Russell et al, 1967 (J Immunol 99, 285–290). Parent viruses listed in Table 1 were used to measure the plaque reduction 50% endpoint (PRNT50) in serum specimens.

EXAMPLE 1

DEN Virus Modification in PDK Cells and Vaccine Lot Production

DEN virus strains selected for vaccine development had a variety of passage histories prior to PDK passage. In the case of DEN-4 341750 there was just one mosquito passage before inoculation of PDK cell culture, while DEN-1 West Pac 74 strain had a history of twenty FRhL cell passages prior to PDK passage (Table 1). With the exception of DEN-3, all strains adapted after a small number of PDK passages. For DEN-3, additional efforts were required to increase viral input in early passages in order to adapt this strain to PDK cells. As a general case after adaptation to PDK cells, DEN virus titers were found to be in the $10^4$–$10^5$ PFU/ml range. Attempts to increase titers were not successful and alternative cell substrates were sought for vaccine production. DBS-FRhL-2 (FRhL) cells were selected for this purpose for several reasons: 1) DEN viruses replicate to titers of ca $10^6$ PFU/ml allowing manufacture of DEN vaccines in these cells; 2) the cells have been used for the preparation of several DEN vaccines that have been tested in Phase I clinical trials without adverse reactions that may be related to the vaccine cell substrate; 3) FRhL cells are normal, rhesus monkey lung diploid cells that have no tumorigenic potential and are free of reverse transcriptase activity and contaminating agents; 4) since the cells are "normal" diploid cells there is no regulatory or other requirement to purify the vaccines; 5) FRhL cell banks can be established at cell generations usable for vaccine manufacture starting with available, low passage cells. PDK passage therefore provides an excellent model for those who wish to study the empirical process of selective attenuation. But, just as PDK serial passage exerts a cumulative selection process, the further passage in another cell substrate provides its own selective pressure. It is not known whether or not FRhL passage increases or decreases the virulence of virus for humans. The use of stable cell lines that must be fully characterized only one time is appealing. However, the published experience with FRhL cells suggests that these cells may reverse or destabilize biological properties acquired during serial passage in PDK (Halstead et al., 1984, Am J Trop Med Hyg 33, 654–665; Halstead et al., 1984, Am J Trop Med Hyg 33, 666–671; Halstead et al., 1984, Am J Trop Med Hyg 33, 672–678; Halstead et al., 1984, Am J Trop Med Hyg 33, 679–683; Eckels et al, 1984, Am J Trop Med Hyg 33, 679–683).

Adaptation of PDK-passaged viruses to FRhL was uniformly successful for all strains of DEN virus and was not dependent on PDK passage. Viral titers from harvests of FRhL passages 1–4 ranged from $10^5$–$10^6$ PFU/ml. By the third-fourth FRhL passage, vaccine lots of all of the DEN strain set viruses were prepared and tested as listed in Table 2. Data is also provided in Table 2 for the FRhL cell bank testing as well as the master and production seed testing. Results of these tests, required to ensure the safety and the freedom from contamination, were negative, or fell within allowable specifications. For the DEN-4 341750 PDK-20 production seed, monkey neurovirulence tests were performed. Results of this study can be found in Hoke, 1990 (Am J Trop Med Hyg 43, 219–226). The DEN-4 production seed as well as the DEN-4 parent virus that was used for comparison were not neuropathogenic. Whether the remaining candidate DEN vaccines need to be evaluated for neurovirulence remains questionable based on data from this experience as well as other tests of DEN monkey neurovirulence (personal communication).

EXAMPLE 2

Rhesus Monkeys Inoculated with PDK-passaged DEN Viruses

The infectivity of DEN viruses passaged in PDK cells and designated as "strain sets" was compared to parental, unmodified viruses for each serotype. Table 3 lists the results of these studies where the degree of infectivity for monkeys was measured by the number of days of viremia that could be found in sequentially drawn serum two weeks following inoculation. Parental virus inoculation of monkeys resulted in 6.8, 5, 3, and 4.7 mean days of viremia in groups of 3–4 monkeys inoculated with DEN-1, DEN-2, DEN-3, and DEN-4, respectively. For DEN-2 parent, additional data (not shown) has substantiated that infection with measurable viremia is very reproducible over time using similar monkeys and isolation techniques. Unfortunately, only partial data exists on viral titers in monkey sera. Most of the data that exists comes from experience with the DEN-2 parent virus where monkey viremic blood was titrated in mosquito cell culture. Peak viral titers at 4–8 days post inoculation resulted in titers reaching $10^5$ PFU/ml of serum (Putnak et al, 1996, supra).

For each strain set, PDK passage results in modification of DEN virus as shown by reduced capacity of the virus to infect monkeys. For several of the strain sets this was clearly evidenced by the complete lack of viremia at the highest PDK passage. Inoculation of monkeys with DEN-1 at PDK passage 27 resulted in 0 days of viremia in 4 monkeys. This translates to 0 isolations out of a total of 56 bleedings tested. A similar result was found for DEN-3 PDK-20 and PDK-30. At PDK-30 for this virus, all evidence of monkey infectivity was lost, i.e., no viremia and no evidence of seroconversion in the monkeys inoculated with $10^6$ PFU of virus. The DEN-2 strain required the greatest number of PDK passages to attain modification of monkey infectivity. With this virus, at least 40 passages in PDK cell culture were required for reduced viremia. To contrast this experience, the DEN-4 strain 341750 only required 6 passages in PDK cells for a modified monkey infection. For another DEN-1 strain, 1009, even after 50 PDK passages there was no evidence of modified monkey infection when compared to parental virus (data not shown). In conclusion, PDK cell passage appears to be an effective empirical method for modification and attenuation of various DEN isolates. This is an unnatural host for DEN that probably places selection pressure for virus populations that are suited for PDK replication but not necessarily for replication in target cells in monkeys and humans.

Materials and Methods for Candidate Vaccine Studies in Humans

Volunteers.

Healthy male and female volunteers ages 18–45 were examined and screened by a panel of tests, including blood chemistries, hematology, prothrombin time, partial thromboplastin time, urinalysis, rapid plasma reagin antibody, and serology for hepatitis B surface antigen and antibody to HIV. Volunteers were excluded on the basis of persistent significant abnormality or positive test. Female volunteers were eligible to participate if they had a negative pregnancy test within 48 hours of vaccination and were willing to sign a consent form stating that they avoid conception using conventional contraception for the 3 months following vaccination. In addition, volunteers were excluded if they had previous flavivirus immunity, which may affect responses to dengue vaccines [Scott, 1983, J Infect Dis 148, 1055–1060] or a history of allergy to neomycin, streptomycin, or gentamycin. Prior flavivirus immunity was defined as having no detectable hemagglutination inhibition antibodies (at a 1:10 serum dilution) against dengue types 1–4, Japanese encephalitis, or yellow fever and no history of yellow fever vaccine or flavivirus infection.

Volunteers scored $\geq 70\%$ on a written exam designed to test knowledge of all aspects of the clinical trial. Informed consent was subsequently obtained from each volunteer in compliance with US 21 CFR Part 50-Protection of Human Subjects. The clinical protocol conformed to all relevant regulatory requirements, including the Declaration of Helsinki (Protocol), and Army Regulations 70-25-Use of Volunteers as Subjects of Research, and 40-7-Use of Investigational Drugs in Humans and the Use of Schedule I Controlled Substances. The studies were approved by the Human Subject Research Review Board, Office of the Surgeon General, U.S. Army, the WRAIR Human Use Research Committee, and the Institutional Review Board, University of Maryland at Baltimore.

Study Vaccines.

The study vaccines are listed in table 4. Vaccine viruses were passaged repeatedly in primary dog kidney cells and then in fetal rhesus monkey lung (FRhL) continuous diploid cell culture as three terminal passages to prepare seed and vaccine. Each candidate, before trial in volunteers, was confirmed to elicit substantially reduced viremia compared to its wild-type parent virus in vaccinated rhesus monkeys. Adequate attenuation measured by infection of rhesus monkeys indicated that the dengue vaccine strains were appropriate vaccines for human testing.

Immediately before immunization, a vial of lyophilized vaccine was reconstituted with sterile water for injection (USP). After immunization, unused portions of rehydrated vaccine were maintained on ice and titrated within 4 hours in LLC-MK$_2$ cell monolayers (Sukhavachana et al. 1966, Bull WHO 35, 65–66). Each volunteer received between $1.0 \times 10^5$ and $4.5 \times 10^6$ pfu of virus, depending on the candidate vaccine injected (Table 4). The passage history of the individual study vaccines is summarized below.

TABLE 4

WRAIR LIVE ATTENUATED DENGUE VACCINES

| Vaccine | PDK Passage* | Year | Study Site | Number of Volunteers | Dose (×10⁵ pfu) |
|---|---|---|---|---|---|
| Dengue 1 | 27 | 1991 | CVD | 10 | 4.4–45 |
| (45AZ5) | 20 | 1991 1992 | CVD # | 10 | 7.7–38 |
|  | 10 | 1991 1992 | CVD | 9 | 2.8–3.5 |
|  | 0 | 1984 | USAMRIID ## | 2 | ? |
| Dengue 2 | 50 | 1991 | CVD | 3 | 6.8 |
| (S16803) | 40 | 1996 | USAMRIID | 3 | 5 |
|  | 30 | 1991 1992 | CVD | 10 | 5.6–10 |
| Dengue 3 | 20 | 1992 | CVD | 6 | 1.0–1.4 |
| (CH53489) | 10 | 1992 | CVD | 3 | 3.8 |
|  | 0 | 1986 | USAMRIID | 2 | ? |
| Dengue 4 | 20 | 1989 | USAMRIID | 8 | 1.0 |
| (341750) | 15 | 1991 | CVD | 3 | 4.8 |
| TOTAL | 10 | — | — | 69 | — |

*Primary dog kidney passage level
Center for Vaccine Development, University of Maryland, Baltimore
United States Army Medical Research Institute of Infectious Diseases, Frederick, MD Dengue 1 45AZ5 Vaccine:

DEN-1 strain West Pac 74 was isolated from a human case of DEN fever on Nairu Island (Western Pacific) in 1974. The isolate was passaged 20 times in FrhL cell culture and a vaccine lot was prepared. Passages included mutagenization and plaque selection to recover a virus that was attenuated and suitable for human vaccination. Following vaccination of two human volunteers, the decision was made to discontinue use of the vaccine due to DEN illness in one of the volunteers. The vaccine was further attenuated by passage in PDK and FrhL cell cultures. The current, candidate vaccine is DEN-1 45AZ5 PDK-20.

Dengue 2 S16803 Vaccine:

The dengue 2 strain S16803 virus was derived from a Thai virus isolate from a patient with dengue fever. The virus was subjected to a total of 50 PDK passages, with terminal passage in fetal rhesus monkey lung diploid cells (DBS-FRhL-2) for seed and vaccine production. Two vaccine candidates were initially prepared at the 30th and 50th PDK passage levels and selected for testing. Another vaccine candidate was developed at the WRAIR from the same dengue 2 parent strain S16803 virus and produced at the 40th passage level by the Salk Institute (Swiftwater, Pa.).

Dengue Type-3 CH53489 Vaccine:

Dengue type-3 strain CH53489 virus was derived from a Thai strain, passaged 30 times in primary dog kidney (PDK) cells after initial passage in primary green monkey kidney (PGMK) and C6/36 insect cells. Virus from PDK passages 10, 20, and 30 was used to inoculate fetal rhesus monkey lung diploid cell cultures.

Dengue 4 341750 Carib Vaccine:

The dengue 4 vaccine candidate was derived from a Caribbean strain of Dengue 4 (Columbia, 1982), passaged at the University of Hawaii, and manufactured at the WRAIR [Marchette, 1990, Am J Trop Med Hyg 43, 212–218]. Antibody to the parent virus neutralizes other dengue 4 virus strains including H-241, the prototype strain. Attenuation of the human isolate was achieved by passage 20 times in primary canine kidney (PDK) cell cultures.

Study Design.

A standard randomized, single-blind inpatient clinical protocol was used for all pilot studies. The majority of the studies were conducted at the Center for Vaccine Development, University of Maryland, Baltimore Md. The pilot studies of dengue 2 S16803 PDK 40 vaccine and dengue 4 CH341750 PDK 20 vaccine were performed at the Medical Division, United States Army Medical Research Institute of Infectious Diseases (USAMRIID), Ft Detrick, Md.

In the initial clinical studies of a vaccine, the highest available passage for a particular strain was tested first in three volunteers. Symptoms were monitored closely for three weeks, and if the volunteers remained well, the next lower passage was tested. If one or more of the volunteers became ill, testing of lower passages of the vaccine strain was not performed, as it was presumed lower passages were likely to be less attenuated. After testing of all acceptable passage levels in three volunteers, the lowest level that did not cause illness was selected for further testing in up to seven additional volunteers.

To allow careful observation, prevent exposure to extraneous infectious diseases, and to prevent the possible infection of vector mosquitoes, volunteers were confined to the research ward from three days prior to inoculation until 20 days after immunization. All adverse experiences occurring within this period following administration of each vaccine were recorded, irrespective of severity or whether or not they are considered vaccination-related. Acceptable safety of a vaccine was defined in advance as the absence of the following serious adverse events: any severe clinical illness not explained by a diagnosis unrelated to the vaccination; persistent fever (oral temperature of $\geq 38.5°$ C. for 4 determinations over 24 hours, a maximum daily oral temperature of $\geq 38.5°$ C. on three successive days, or temperature exceeds 40° C. on any individual determination); thrombocytopenia (fewer than 100,000 platelets/mm$^3$) or leukopenia (absolute neutrophil count<1000) on 2 consecutive determinations; or serum amino alanine transferase (ALT) level of more than 4 times normal on 3 or more successive days which is otherwise unexplained. In addition, any experience which would suggest any significant side effect that may be associated with the use of the vaccine were documented as a serious event.

Volunteers were inoculated subcutaneously with 0.5 ml of undiluted vaccine on day 0. After immunization, vital signs were recorded every 6 hours. The injection site was examined and the maximum diameter of erythema and induration measured and recorded daily. Clinical signs (fever [>37.8° C.], rash, vomiting, petechiae, and liver and splenic enlargement) and symptoms (malaise, headache, myalgia, arthralgia, nausea, and eye pain or photophobia) were assessed daily for the first 20 days after immunization. Symptoms were graded as mild (noticed symptom but continued ward activity) or severe (forced to bed by symptom). If requested by the volunteer, painful symptoms were treated with propoxyphene hydrochloride; antipyretics were not used. Observations were recorded on a standard checklist of symptoms and physical findings. Volunteers were discharged from the study ward on day 21, and requested to return for serologic studies 1, 6, 12, and 24 months after inoculation.

Two healthy flavivirus-immune volunteers were immunized at USAMRIID with the parent strain of the dengue 1 45AZ5 vaccine and two years later with the parent strain of the dengue 3 CH53489 vaccine. Medical records from the study were reviewed for presence or absence of the following signs and symptoms: fever, rash, malaise, headache, myalgia, arthralgia, and eye pain or photophobia. Viremia was measured daily. In contrast to the present trials, symptoms were not systematically recorded, and the intensity of symptoms was not graded. In addition, clinical experience with the dengue 4 341750 Carib PDK 20, given to 8 volunteers at USAMRIID during a later study, was extracted and summarized to compare with those of the current vaccinees [Hoke, 1990, supra].

Laboratory Evaluation.

Blood was collected from volunteers every other day and on day 31 for routinely available medical tests for hemoglobin and hematocrit, white blood cell count with differential count, platelet count, and aspartate aminotransferase (AST) and alanine aminotransferase (ALT) levels. In addition, blood was collected every other day through day 20 for virus isolation and antibody studies. Blood (20 ml) was allowed to clot at 4° C. for <2 hours, sera was decanted into 1-ml aliquots, frozen and stored at −70° C. until study.

Virus Isolation. For determination of dengue viremia, serum was thawed and inoculated onto C6/36 mosquito cell monolayers and incubated at 28° C. for 14 days. Supernatant culture fluid harvests were assayed for virus by plaque assay on LLC-MK$_2$ cells (Sukhavachana et al. 1966, Bull WHO 35, 65–66). To quantitate the amount of virus in serum, a plaque assay was performed on the C6/36 clone of Aedes albopictus mosquito cells [Hoke, 1990, supra]. Cell culture flasks were inoculated with dilutions of plasma and adsorbed at 35° C. for 1–2 hours. An overlay medium consisting of Hank's Balanced Salt Solution and 0.75% agarose, 5% lactalbumin hydrolysate, 0.12 M NaHCO$_3$, and antibiotics was added and all flasks were incubated at 35° C. After 7 days, the flasks were stained with 5% liquid neutral red for 3–5 hours. Excess stain was removed and the plaques read after 18 hours.

Serology.

Antibody tests included ELISA, HAI, and plaque reduction neutralization tests (PRNT) performed using a dengue virus of the same serotype as the strain in the vaccine being tested. Detection of anti-dengue IgM antibodies was performed by modification of an ELISA, where values >0.10 OD units were considered positive [Innis, 1989, supra]. The HAI test was performed by the standard technique modified to microvolumes using 4–8 units of individual antigens, using serum extracted with acetone to remove inhibitors [Clarke and Casals, 1958, Am J Trop Med Hyg 7, 561–573]. PRNT assays were performed by the method described by Russell et al.[Russell, 1967, supra].

Statistical Analysis.

The relationship between passage level and the frequency and severity of reactogenicity was analyzed, for dengue 2 vaccine S16803 (PDK 30, 40 and 50) and for dengue 3 vaccine CH53489 (PDK 10 and 20), using the Cochran-Armitage test for trend and Spearman's correlations, respectively. The symptoms and signs independently analyzed included the presence or absence, and the number of days experiencing eye symptoms, headache, malaise, myalgia, arthralgia, rash and fever (temperature>37.8° C.). The null hypothesis, that higher PDK level was not associated with lower reactogenicity, was evaluated at a probability of five percent. By inspection of the data, the optimal passage level for each virus was determined based on the clinical and immunological responses of each volunteer. The passage level which caused no unacceptable side effects but which immunized about 80% of volunteers was selected for further development by the U.S. Army Medical Research and Development Command's Flavivirus Vaccine Steering Committee.

Definition of Infection by the Vaccine

Infection by vaccine is defined as replication of dengue virus in the volunteer, detected by presence of serum type-specific neutralizing antibody or IgM anti-dengue antibody after immunization. Viremia was not included as necessary for diagnosis of infection as it was never detected in the absence of an antibody response. A vaccine failure is defined as an unacceptable adverse clinical response or failure to develop convalescent IgM or PRNT antibodies.

EXAMPLE 3

Clinical Responses to Attenuated Dengue Vaccines
Dengue 2 S16803 Vaccine

The dengue 2 strain S16803 virus produced from the 50th passage in PDK cells was tested in three volunteers. The volunteers did well, with no oral temperatures>38.0° C. Two of 3 volunteers had transient mild symptoms of malaise, headache, and eye symptoms (eye pain or photophobia). Laboratory findings included mild ALT elevations (<2×normal) in 2 of 3, and mild leukopenia in 1 of 3 volunteers. Because of the acceptable safety profile of the PDK 50 vaccine, the next lower available passage, PDK 30, was selected for clinical evaluation.

The PDK 30 vaccine, tested in 10 subjects, was underattenuated and produced symptoms compatible with mild to moderate dengue. Four volunteers (40%) developed low grade fever, to Tmax 38.5° C., over days 9–14 post vaccination (median day 12). Eighty percent developed rash. The majority of volunteers experienced eye symptoms (10/10), headaches (9/10), and malaise (9/10), while 70 percent had ≧1 severe symptom of headache, eye pain and photophobia, malaise, or myalgia. Three volunteers had mild elevation of their alanine aminotransferase (ALT), a measure of liver pathology.

Because the PDK 30 vaccine was considered too reactogenic to test further in volunteers, the PDK 40 vaccine was produced from the master seed. Two of three volunteers inoculated with PDK 40 developed a mild dengue-like syndrome 9–10 days after vaccination, with low-grade temperatures (<38.1° C.), rash, myalgias, and headache. Symptoms resolved spontaneously over several days without disability or requirement for medication. Accompanying symptoms was an unanticipated rise in serum liver enzymes, to a maximum ALT level of 199 IU/ml in one (4 times normal) and 77 IU/ml maximum ALT for the other (1.5 fold elevation from normal). The third volunteer remained asymptomatic but also developed two-fold elevations in ALT (to max $10^2$). All laboratory abnormalities resolved within days without intervention, and all volunteers were discharged in good health 21 days after receipt of the vaccine. Because of the unusual frequency of hepatitis events associated with PDK 40 vaccine, no further development is planned for the product.

TABLE 5

Clinical Responses in Recipients of Dengue 2 S16803 Virus Vaccines

| Passage Level | malaise | headache | myalgia | arthralgia | eye sx | rash | fever T>37.8∞C. | days of fever (median) | max fever |
|---|---|---|---|---|---|---|---|---|---|
| 2-S16803-30 | 9/10 | 9/10 | 7/10 | 4/10 | 10/10 | 8/10 | 4/10 | 9–14 (12) | 38.5 |
| 2-S16803-40 | 2/3 | 2/3 | 2/3 | 1/3 | 1/3 | 2/3 | 1/3 | 8, 9 | 38.0 |
| 2-S16803-50 | 2/3 | 2/3 | 0/3 | 1/3 | 2/3 | 0/3 | 0/3 | — | — |

Symptom-days

| Passage Level | malaise | headache | myalgia | arthralgia | eye sx | rash | fever T>37.8∞C |
|---|---|---|---|---|---|---|---|
| 2-S16803-30 | 2.2 | 3.6 | 2.4 | 1.7 | 3.3 | 5.4 | 0.5 |
| 2-S16803-40 | 2.0 | 1.7 | 2.0 | 1.0 | 5.7 | 1.7 | 0.7 |
| 2-S16803-50 | 0.6 | 0.7 | 0.0 | 0.3 | 1.0 | 0.0 | 0.0 |

TABLE 6

Clinical Responses in Recipients of Dengue 3 CH53489 Virus Vaccines

A: Number of patients having response

| vaccine | malaise | headache | myalgia | arthralgia | eye sx | rash | T>37.8° C. (days) | max fever |
|---|---|---|---|---|---|---|---|---|
| 3-CH53489-0 | 2/2 | 2/2 | 2/2 | 1/2 | 2/2 | 2/2 | 2/2 (5–9) | 40.6 |
| 3-CH53489-10 | 1/3 | 2/3 | 2/3 | 1/3 | 1/3 | 2/3 | 1/3 (10, 11) | 38.2 |
| 3-CH53489-20 | 3/6 | 5/6 | 3/6 | 4/6 | 4/6 | 1/6 | 1/6 (3) | 38.7 |

B: Symptom days

| vaccine | malaise | headache | myalgia | arthralgia | eye sx | rash | T>37.8° C. (days) |
|---|---|---|---|---|---|---|---|
| 3-CH53489-0 | 3.5 | 4.0 | 4.5 | 2.0 | 3.5 | 7.5 | 5.0 |
| 3-CH53489-10 | 0.3 | 3.3 | 2.3 | 1.0 | 1.3 | 6.3 | 0.7 |
| 3-CH53489-20 | 1.7 | 2.8 | 1.0 | 2.0 | 1.3 | 0.8 | 0.2 |

TABLE 7

Viremia and Immune Responses to Dengue Vaccines

| Vaccine and passage level | viremia | days of viremia (median) | range titer | seroconversion IgM | HAI | PRNT | GMT31 | GMT60 |
|---|---|---|---|---|---|---|---|---|
| 2-16803-30 | 10/10 | 6–12 (10) | 3–1200 | 8/10 | 6/9 | 10/10 | 343 | 262 |
| 2-16803-40 | 2/3 | 6–10 (8) | NA | 3/3 | 2/3 | 3/3 | 640 | 618 |
| 2-16803-50 | 0/3 | — | — | 1/3 | 1/3 | 2/3 | 11 | 13 |
| 3-53489-0 | 2/2 | 3–10 (6) | NA | 2/2 | 2/2 | 2/2 | 2818 | 1995 |
| 3-53489-10 | 2/3 | 6–10 (8) | 84–6600 | 1/3 | 3/3 | 3/3 | 710 | 153 |
| 3-53489-20 | 2/6 | 8–12 (10) | 12–138 | 2/6 | 1/6 | 3/6 | 556 | |
| 4-341750-15 | 1/3 | 8–10 (9) | 3–15 | 3/3 | 3/3 | 3/3 | | |
| 4-341750-20 | 5/8 | 8–14 (10) | 10–1200 | 5/8 | 5/8 | 5/8 | | 160 |

TABLE 8

Results of Phase I Trials of WRAIR Dengue Vaccine Candidates

| Vaccine | PDK Passage[a] | Mean Days viremia | Mean Illness Score | Acceptable Reactogenicity | Number Infected[b] | Number Seroconverted[c] | Range % Seroconversion |
|---|---|---|---|---|---|---|---|
| Dengue 1 | 27 | 0.0 | 2.4 | Yes | 7 (70%) | 4 (40%) | 3–77 |
| (45AZ5) | [20] | 1.0 | 3.6 | Yes | 10 (100%) | 10 (100%) | |
| | 10 | 5.0 | 3.9 | Yes | 7 (78%) | 7 (78%) | |
| Dengue 2 | [50] | 0.0 | 5.0 | Yes | 2 (67%) | 2 (67%) | |
| (S16803) | 40 | 1.7 | 14.7 | No | 3 (100%) | 3 (100%) | |
| | 30 | 2.2 | 19.1 | No | 10 (100%) | 10 (100%) | |
| Dengue 3 | [20] | 0.6 | 11.0 | Yes | 3 (50%) | 3 (50%) | |
| (CH53489) | 10 | 2.3 | 15.3 | No | 3 (100%) | 3 (100%) | |

TABLE 8-continued

Results of Phase I Trials of WRAIR Dengue Vaccine Candidates

| Vaccine | PDK Passage[a] | Mean Days viremia | Mean Illness Score | Acceptable Reactogenicity | Number Infected[b] | Number Seroconverted[c] | Range % Seroconversion |
|---|---|---|---|---|---|---|---|
| Dengue 4 (341750) | [20] 15 | 3.8 0.6 | 6.6 20.7 | Yes No | 5 (63%) 3 (100%) | 5 (63%) 3 (100%) | |

[a]Primary dog kidney passage level
[b]Defined as anti-dengue IgM positive or PRNT50 seroconversion
[c]Defined as a neutralizing antibody titer >1:10 (PRNT50)
[ ] Strain proposed for expanded clinical study Table 5 summarizes the initial clinical experience with the WRAIR dengue 2 vaccine.

Decreased frequency of signs of fever and rash are apparent between passage level 30 and 50 vaccines. Furthermore, there is a decline in oral temperature from Tmax 38.5° C. towards normal with increasing passage, but no change in duration of fever beyond one day. For the dengue 2 vaccine, the frequency and duration of eye symptoms, rash, headache, malaise and myalgia were significantly associated with passage level.

Dengue 3 CH53489 Vaccine.

A dengue 3 vaccine (CH53489, PDK 0) developed at WRAIR was administered to two healthy yellow fever-immune male volunteers as a 0.5 ml subcutaneous inoculation of $2 \times 10^4$ pfu of virus. The immediate post immunization course was uneventful. By day 6, both volunteers were ill with moderately severe dengue fever characterized by high fever, chills, myalgias, headache, malaise, and a diffuse erythematous rash. Both volunteers developed thrombocytopenia and leukopenia but there were no signs of hemorrhagic fever. After a febrile period lasting five days, both men rapidly recovered and were well by day 21. Because of the severe illnesses experienced by both subjects, no further testing of this passage level was undertaken. Subsequently, PDK 10 and PDK 20 passage levels were prepared as vaccine candidates.

The PDK 20 vaccine was given to 6 volunteers and resulted in mild reactogenicity. One subject experienced an early febrile illness on day 3 with transient fever (Tmax 38.2° C.), pharyngitis, and cervical lymphadenopathy. No dengue virus was isolated from the volunteer's serum. This subject was felt to have had an intercurrent illness with fever, which was not directly related to vaccination. Four out of 6 volunteers developed short-lived mild dengue symptoms without rash; arthralgia, eye pain, and headache were the most frequent complaints. However, one volunteer had more severe symptoms of headache, malaise, and eye pain for three days. He also developed leukopenia and sustained elevation in ALT levels; these laboratory abnormalities had resolved on follow-up at day 31. Another volunteer had mild and reversible elevation of ALT alone, to less than 2x normal. Because the PDK 20 vaccine was safe with marginally acceptable reactogenicity, the next lowest available passage vaccine virus (PDK 10) was tested.

The PDK 10 virus proved too reactogenic in recipients. One of three volunteers developed low-grade fever on days 10 and 11 (Tmax 38.3° C.), and a florid rash for 13 days. Another volunteer developed persistent pruritus associated with waxing and waning hives on days 6 to 9 post vaccination, and tender cervical and axillary lymph nodes. He subsequently developed a maculopapular rash with malaise, headache, and myalgia on days 10–12. This volunteer may have had an idiosyncratic allergic reaction to the vaccine, followed by a typical dengue-like illness. These two volunteers also had laboratory abnormalities of leukopenia and elevation of ALT levels to <2x normal, which resolved on followup on day 31.

Table 6 summarizes the response to dengue 3 CH53489 vaccines. Although there was a trend for less frequent and shorter duration signs and symptoms with passage, no passage reached statistical significance in either analysis.

Dengue 4 341750 Vaccine.

Eight volunteers received $10^5$ PFU of PDK 20 vaccine (Hoke, 1990 supra). Five volunteers developed a scarcely noticeable macular, blanching rash and minimal temperature elevation (max 38.1° C.). Viremia and antibody response also developed in these five volunteers (63%).

A new DEN-4 341750 candidate vaccine was prepared from PDK passage 15, anticipating that the lower passage might be more infective. Three volunteers received this vaccine and two experienced minimal symptoms. The third volunteer became ill abruptly on day 8 with fever, edematous swelling of the face and extremities, severe lassitude, rash, eye pain, photophobia, and arthralgias. Over the next three days, fever persisted with Tmax of 39.6° C., but signs and symptoms resolved spontaneously. Because of this serious adverse reaction to vaccination, further use of PDK-15 vaccine was terminated and PDK-20 was chosen for further evaluation.

EXAMPLE 4

Viremia and Immune Responses to Attenuated Dengue Vaccines

Table 7 describes viremia and immune responses with the WRAIR dengue vaccines. The infectivity of the individual vaccines is summarized below.

Dengue 2 S16803 Vaccine.

No recipients of the PDK 50 vaccine developed viremia, yet two of 3 developed low-titer neutralizing antibody by day 60. These findings suggested that the vaccine virus was diminished in infectivity for humans. By contrast, two of 3 dengue 2 PDK 40 vaccinees had demonstrable viremia, and all developed high titer antibody after vaccination. As expected, infectivity of the dengue 2 PDK 30 vaccine was highest: viremia was detected in all 10 volunteers and all subjects seroconverted with neutralizing antibody titers of >1:60 by day 60.

Dengue 3 CH53489 Vaccine.

Dengue-3 virus retaining temperature sensitivity and small plaque phenotype of the vaccine virus was recovered for 6 and 7 days in the 2 yellow fever immune recipients of the dengue 3 PDK 0 vaccine. Subsequently, high titered PRNT50 and hemagglutination inhibition (HAI) antibodies with a secondary-infection-like cross reactivity was measured in serum collected on days 30 and 60 from both volunteers. Infectivity was similar in subjects who received the dengue 3 PDK 10 attenuated vaccine: 2 of 3 developed viremia and vaccination induced neutralizing antibodies in all. In contrast, 2 of 6 dengue 3 PDK 20 vaccinees had detectable viremia and three volunteers subsequently seroconverted, reflecting diminished infectivity.

Dengue 4 341750 Vaccine.

Eight volunteers received $10^5$ PFU of the PDK 20 vaccine, and viremia and antibody response developed in five (63%). The vaccine prepared from a lower passage of this candidate, PDK 15, was more infective. Virus was isolated from a single volunteer, on days 8 and 10 following vaccination, with maximum titer of 15 pfu/ml. This volunteer subsequently developed a neutralizing antibody titer of 450 with a secondary HAI response, and was found to have been previously exposed to St. Louis encephalitis virus (PRNT titer 1:20 before vaccination). The two volunteers without detectable viremia developed neutralizing titers of 1:10 and 1:40 by day 30 after vaccination.

EXAMPLE 5

Selection of Candidate Vaccines

The extended program of safety testing of the WRAIR PDK-attenuated vaccines is shown in Table 8, which lists the salient features of the vaccines for each serotype. Increasing PDK passage resulted in decreasing mean illness score, which assesses duration and number of symptoms per volunteer. In addition, rising PDK passage was also associated with decreased mean days of viremia, with the exception of dengue 4 vaccines. Of the tested dengue 2, 3, and 4 vaccines, only one passage level was judged safe and acceptably reactogenic, and suitable for expanded clinical study: dengue 2 PDK 50, dengue 3 PDK 20, and dengue 4 PDK 20. However, the percentage of recipients infected declined with increasing PDK passage level. Seroconversion, defined as percentage with neutralizing antibody titer ≧1:10 similarly declined within broad confidence intervals.

DISCUSSION

The WRAIR has longstanding involvement in the development of live-attenuated dengue vaccines. Both the WRAIR and Mahidol dengue vaccine programs have developed several live vaccines by attenuation through several passages (repeated growth in tissue culture) in dog kidney (PDK) cells. The results of the pilot testing in small numbers of volunteers established the safety of WRAIR candidate vaccines. No volunteers among 65 recipients required emergent treatment of sustained serious injury. Three volunteers suffered transient idiosyncratic reactions associated with dengue vaccination, resulting in withdrawal of the vaccines they received from further clinical development. Experimental infection with underattenuated vaccines, while uncomfortable, was tolerable.

The clinical experience showed that increasing PDK passage of vaccine viruses increased attenuation for volunteers. This effect is best seen with dengue 1 and dengue 3 viruses, where parental unpassaged viruses resulted in unmodified dengue fever and subsequent 20 PDK passages acceptable reactogenicity. However, increasing PDK passage decreased infectivity of vaccine viruses, resulting in diminished immunogenicity. Furthermore, diminished viremia with vaccine viruses in humans appear to correlate with those in rhesus monkeys (with the exception of dengue 4 PDK 15). These findings suggest that infectiousness of an attenuated dengue virus vaccine in volunteers proved equivalent to immunogenicity. The relationship between passage level and reactogenicity should be interpreted with caution, because subjects who experienced one symptom were likely to experience several symptoms. As our analytic methods assume independence of these symptoms, interpretations based on independent p-values can be tenuous. Still, we believe rash showed a strong association with passage level (independent p=0.009 for presence, p=0.01 for duration). This is bolstered by a lack of significant correlation between rash and other symptoms, for either Dengue 2 or 3 vaccine (Spearman's tests).

Only vaccines with acceptable safety profiles were selected for expanded clinical testing: dengue 1 45AZ5 PDK 20, dengue 2 S16803 PDK 50, dengue 3 CH53489 PDK 20, and dengue 4 341750 PDK 20. Because of the broad confidence intervals in seroconversion due to small numbers of volunteers, subsequent studies sought to increase the number of recipients of each of the four selected vaccines. In addition, further tests will seek to determine whether immunogenicity of these attenuated vaccines can be boosted through administration of two doses instead of the single dose used for these studies.

What is claimed is:

1. A method for replicating dengue virus to a titer growth of at least $10^5$ PFU/ml, wherein the dengue virus is selected from the group consisting of the dengue-1 strain identified as 45AZ5 PDK20 and given the ATCC accession no. VR-2648; the dengue-2 strain identified as S16803 PDK50 and given the ATCC accession no. VR-2653, the dengue 3 strain identified as CH53489 PDK20 and given the ATCC accession no. VR-2647, and the dengue 4 strain identified as 341750 PDK20 and given the ATCC accession no. VR-2652, comprising the step of infecting cells from a continuous epithelial or fibroblast cell line with a growth strain having a titer growth of at least $10^5$ PFU/ml, wherein said continuous epithelial or fibroblast cell line lacks contaminating adventitious agents such that cells from said cell line are suitable for use in mammalian virus vaccine production.

2. The method of claim 1 wherein the dengue virus is chosen from the group consisting of: dengue 1, dengue 2, dengue 3, and dengue 4.

3. The method according to claim 2 wherein said dengue virus is attenuated.

4. The method of claim 1 wherein said cells are Vero cells.

5. The method of claim 4 wherein said Vero cells have a passage number of 20–190.

* * * * *